United States Patent [19]

Genese

[11] 4,381,006
[45] Apr. 26, 1983

[54] CONTINUOUS LOW FLOW RATE FLUID DISPENSER

[75] Inventor: Joseph N. Genese, Waukegan, Ill.

[73] Assignee: Abbott Laboratories, North Chicago, Ill.

[21] Appl. No.: 205,825

[22] Filed: Nov. 10, 1980

[51] Int. Cl.³ .............................................. A61M 5/00
[52] U.S. Cl. ...................... 128/218 A; 128/DIG. 12; 222/340
[58] Field of Search ........... 128/214 F, 218 F, 218 A, 128/215, 273, DIG. 12; 222/340

[56] References Cited

U.S. PATENT DOCUMENTS

| | | | |
|---|---|---|---|
| 1,039,591 | 9/1912 | Prideaux | 128/218 F |
| 3,415,419 | 12/1968 | Jewett et al. | 222/76 |
| 3,451,393 | 6/1969 | Sarnott | 128/214 F |
| 3,456,649 | 7/1969 | Jewett et al. | 128/214 |
| 3,630,417 | 12/1971 | De Haas | 222/333 |
| 3,670,926 | 6/1972 | Hill | 128/214 F |
| 3,675,651 | 7/1972 | Meyer | 128/215 |
| 3,886,938 | 6/1975 | Szabo et al. | 128/218 A |
| 3,901,231 | 8/1975 | Olson | 128/214 F |
| 3,923,426 | 12/1975 | Theeuwes | 417/48 |
| 4,085,747 | 4/1978 | Lee | 128/214 F |
| 4,132,231 | 1/1979 | Puccio | 128/214 F X |
| 4,139,008 | 2/1979 | Wagner | 128/215 |
| 4,202,333 | 5/1980 | Thill et al. | 128/218 A |

FOREIGN PATENT DOCUMENTS 2437216  5/1980  France ......................... 128/218 A Primary Examiner—Dalton L. Truluck
Attorney, Agent, or Firm—Robert L. Niblack; Neil E. Hamilton

[57] ABSTRACT

A continuous low flow rate dispenser of the syringe type wherein a fluid medicament can be administered at a slow and controlled rate to a patient over a long period of time. A syringe carrier having biasing means in the form of spiral coiled springs will be placed under tension as an abutment member is moved away from an opposing slidable driver member. A standard syringe has the plunger moved to an activated position and placed in the syringe carrier with the abutment member in contact with the engagement surface at the end of the plunger rod and the opposing slidable driver member in contact with the engagement surfaces (finger flanges) on the barrel member. A control means is placed in a closed position which will hold the fluid medicament in the syringe barrel but under the biased tension of the biasing means. Upon opening of the control means, the abutment member and the slidable driver member will be moved toward each other, thereby forcing the plunger stopper toward the nozzle portion to expel the fluid from the barrel member at a slow and steady rate.

8 Claims, 6 Drawing Figures

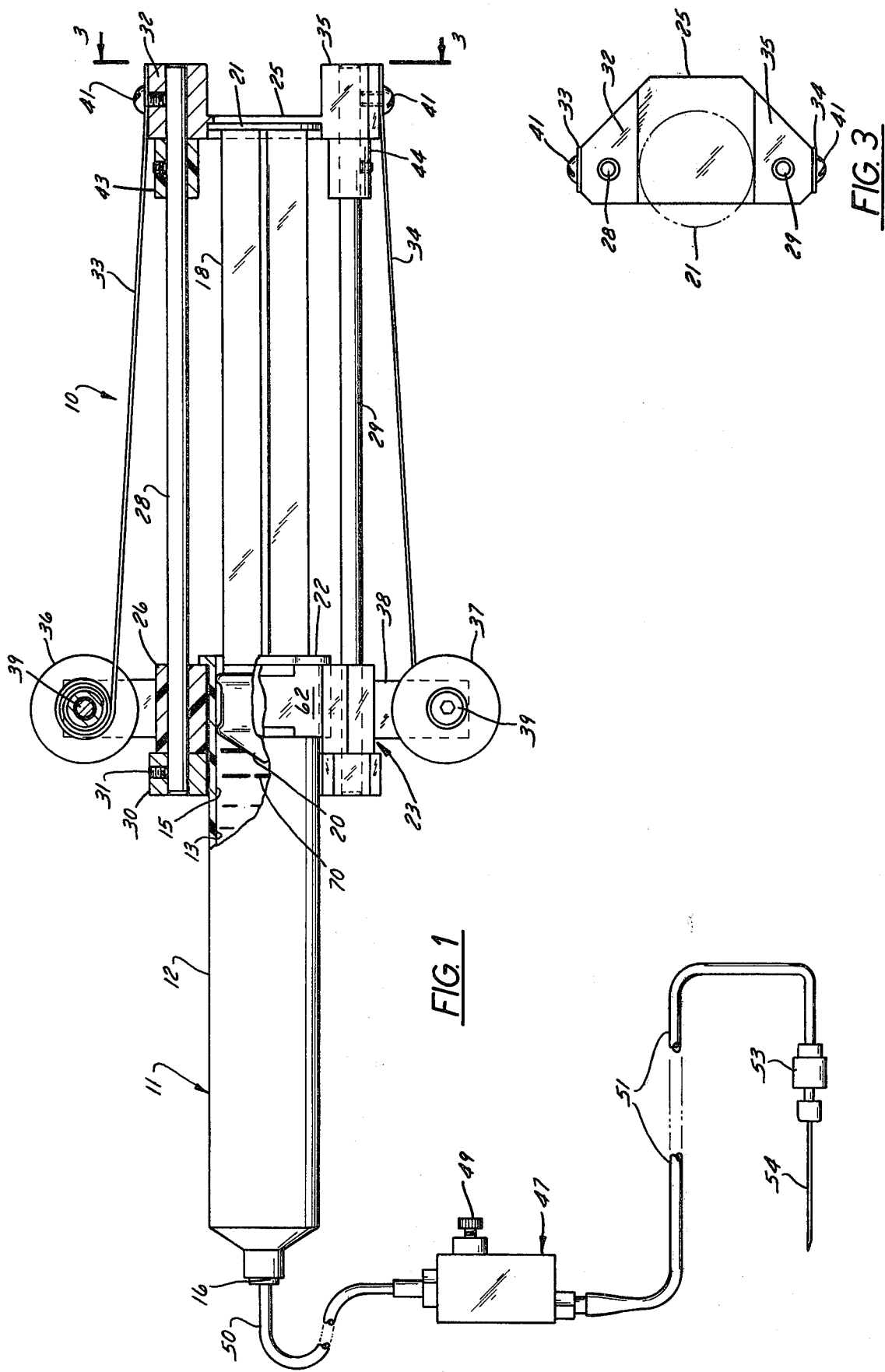

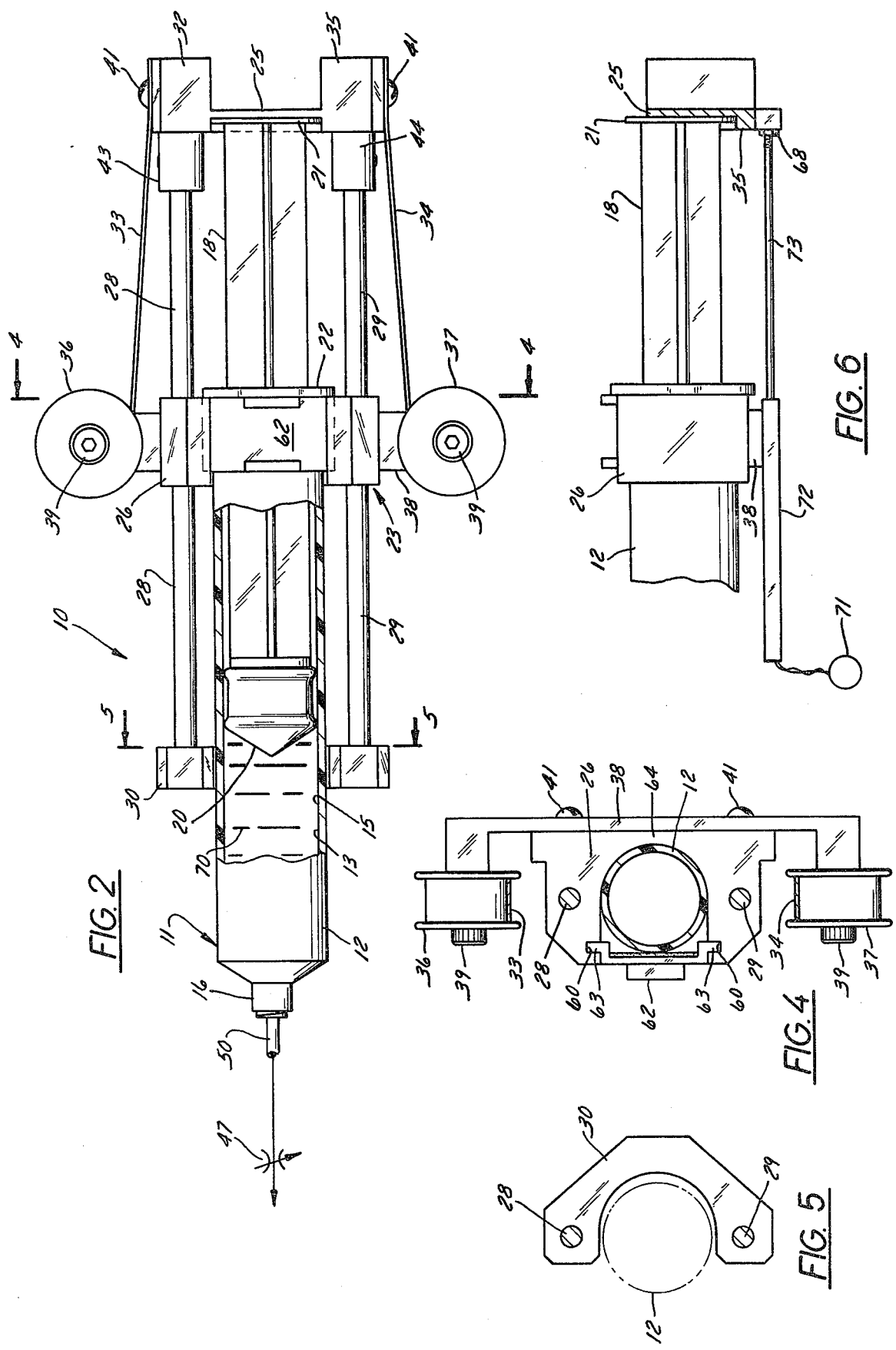

4,381,006

CONTINUOUS LOW FLOW RATE FLUID DISPENSER

BACKGROUND OF THE INVENTION

This invention relates to a dispenser which can administer a fluid material at a continuous low flow rate. More particularly, it relates to a syringe system wherein a standard syringe can be activated and placed in a syringe carrier member which includes a biasing means to provide upon opening of a control means, a slow and steady discharge of the fluid contents of the syringe, which in this manner is commonly referred to as an "ooz pump."

The prior art affords many pump units which can administer the contents thereof at a slow and steady rate. For example, in U.S. Pat. No. 4,202,333, a dispensing device of the type concerned with in this invention is disclosed wherein the contents of the syringe are expelled by a spring member activated in conjunction with the cover of the unit. In U.S. Pat. Nos. 3,415,419; 3,456,649; 3,630,417; 3,901,231; 4,139,008; and 4,085,747, all describe fluid administration type pumps for administering controlled dosages of medicament and utilize power operated mechanisms. In U.S. Pat. No. 3,886,938, an escapement mechanism is employed in a power operated fluid infusion device, whereas in U.S. Pat. No. 3,923,426, an electroosmotic pump is utilized.

Nowhere in the prior art is there provided a fluid dispensing device which can utilize a standard I.V. administration syringe and effect a delivery thereof in a precise and controlled manner. The prior art is either concerned with power operated units; those which require a multiplicity of components; or which require specially designed components.

It is an advantage of the present invention to provide a continuous low flow rate fluid dispensing unit which utilizes a standard I.V. syringe, yet will deliver the contents of the syringe in a precise and accurate manner. Other advantages are an ooze pump which is fabricated from a minimum number of parts; is operable without the need of an external energy power source; and can, if desired, be activated simultaneously with the filling of the syringe.

SUMMARY OF THE INVENTION

The foregoing advantages are accomplished and the shortcomings of the prior art are overcome by the present syringe device which will deliver the contents thereof at a slow and steady rate. The syringe device includes the usual barrel member for a standard syringe, having a substantially tubular chamber with an internal wall and a nozzle portion. The standard plunger member including a rod has a sealing member or stopper secured thereto at one end and an engagement surface at the other is utilized with the sealing member in slidable engagement with the internal wall and the plunger rod positioned for reciprocal movement into and out of the barrel. Engagement surfaces in the form of finger grips extend from the barrel member. A syringe carrier member has an abutment member for contact with the engagement surface of the plunger rod and a slidable driver member is constructed for contact with the engagement surfaces of the barrel on the side opposite the abutment member. Guide means are provided for the driver member and extend from the carrier abutment preferably on opposite sides of the barrel and longitudinally thereof. Biasing means extend between the slidable driver member and the abutment member while control means of the fluid passage type are operatively associated with the nozzle portion which has a length of tubing extending therefrom.

In one manner of operation, upon opening of the fluid passage in the control means and movement of the plunger rod out of the syringe barrel, fluid material will be aspirated into the barrel from the tubing and the biasing means will be placed under tension. Upon closing of the control means, the fluid will be retained in the syringe barrel so that upon subsequent opening of the control means, the slidable carrier driver member and the carrier abutment surface will be forced in opposing directions to thereby move the plunger stopper toward the nozzle portion to expel the fluid material from the barrel member and out through the tubing at a slow and steady rate.

In a preferred manner, the biasing means is of the spiral coiled spring type and the biasing means further includes rotatable retracting members carried by the slidable driver member with the spiral coiled springs being operatively secured to the rotatable members at one end and fastened to the carrier abutment member at the other. The guide means are preferably in the form of rod members extending from the carrier abutment member, with the slidable driver including bearing surfaces for slidable contact with the rod members, the rod members being interconnected at their ends opposite the carrier by a stabilizing member having an open portion to accommodate the syringe barrel. The control means is of the manually operable type and when the syringe is utilized to deliver an I.V. fluid, a hypodermic needle will be secured to the tubing.

BRIEF DESCRIPTION OF THE DRAWING

A better understanding of the continuous low flow rate fluid dispensing device of this invention will be provided by reference to the drawing wherein:

FIG. 1 is a view in side elevation with parts broken away, illustrating the fluid dispensing unit of this invention.

FIG. 2 is a view similar to FIG. 1 except not showing the control means, and illustrating the unit in an intermediate operating position.

FIG. 3 is an end view, taken along line 3—3 of FIG. 1.

FIG. 4 is a view in vertical section taken along line 4—4 of FIG. 2.

FIG. 5 is a view in vertical section taken along line 5—5 of FIG. 2.

FIG. 6 is a partial view showing a means of measuring the fluid delivered from the fluid dispensing unit.

DESCRIPTION OF THE PREFERRED EMBODIMENT

Referring to FIGS. 1-3 of the Drawings, the syringe unit, generally 10, utilizes a standard syringe 11 which includes a barrel member 12 having a substantially tubular chamber 13 with an internal wall 15 and a nozzle portion 16. A plunger rod 18 has a stopper 20 secured thereto at one end and the usual engagement portion 21 at the opposite end. The syringe 11 also has the usual opposing finger grips providing engagement surfaces 22. A syringe carrier generally 23 accommodates syringe 11 and provides an abutment member 25 for contact with engagement portion 21 of the plunger rod 18. A slidable driver member 26 is positioned for contact with engagement surfaces 22 and is slidably guided over guide rods 28 and 29. The guide rods 28 and 29 are secured in block portions 32 and 35 of abutment member 25 at the opposing ends in a stabilizer member 30 which fastening is afforded by set screw 31. This is indicated in FIGS. 1 and 5. Two spiral coil springs 33 and 34 are fastened to block members 32 and 35 by means of screws 41, which also secures the rod members 28 and 29 in the respective blocks 32 and 35. The spiral coil springs are operatively secured to rotatable retracting members 36 and 37 and are carried by a bracket member 38 with axle 39 affording the usual rotatable attachment. It will also be noted that two spacing members 43 and 44 are also fastened on rods 28 and 29 so as to afford suitable spacing between abutment member 25 and the slidable driver member 26 when the syringe system is initially assembled with the spiral coil springs 33 and 34 affording an initial biasing on the slidable driver member, even in the inactivated position. A control means 47 in the form of the variable restrictor type, is in fluid communication with nozzle 16 through tubing 50. The control means has a rotatable control knob 49 for adjusting the rate of fluid therethrough. Extending from the opposite end of the control unit 47 is another length of tubing 51 interconnected to the needle adapter 53 of the Luer type for connection with hypodermic needle 54.

As best seen in FIG. 4, a generally U-shaped retaining member 62 is accommodated in slidable driver member 26 which is accomplished by slots 60 for accommodating flanges 63 on member 62. Retainer 62 will contact one of the engagement surfaces 22 while an opposing side wall portion, such as indicated at 64, will contact an opposing one.

OPERATION

A better understanding of the advantages of the syringe unit 10 will be had by a description of its operation.

Syringe carrier 23 will initially have slidable driver 26 moved against spacing members 43 and 44 as spiral coiled springs 33 and 34 will be under a slight biasing force through the action of rotatable retracting members 36 and 37. U-shaped retainer 62 will have been removed from slidable member 26 and barrel member 12 will be placed therein with engagement portion 21 of plunger 18 seated against abutment member 25 as illustrated in FIGS. 1 and 3. Retainer 62 will be slidably replaced as shown in FIG. 4. Control means 47 will be placed in an open position and plunger 18 will be pulled outwardly from barrel member 12 so as to aspirate the desired I.V. fluid 70 into the syringe barrel. As this is effected, an increased biasing force will be provided between slidable driver 26 and abutment member 25. When a sufficient quantity of liquid is aspirated into the syringe barrel 12, the fluid control member 47 will be closed. The resulting biasing means will cause an increased force to be exerted between the driver 26 and the abutment member 25 so as to force plunger 18 into the syringe barrel 12. However, movement will be restricted because of the closing of the flow control 47.

When it is desired to administer the I.V. fluid 70, a suitable venipuncture will be made by means of the hypodermic needle 54 and the control 47 will be opened to a degree which will permit a slow flow of fluid to be expelled from the needle 54. The flow will be steady and at a continuous rate as the driver 26 and the abutment member 25 are pulled toward each other through the action of spiral coiled springs 33 and 34. The flow control can be adjusted so that this delivery is effected over a period of about 10 hours. It will be noted that driver 26 will effect a smooth and steady delivery of the contents of the syringe as it is guided along the longitudinal length of the syringe barrel by guide rods 28 and 29.

In the previous description, the biasing means as represented by spiral coiled springs 33 and 34 as well as retracting members 36 and 37 are actuated simultaneously with the filling of syringe 11. Alternatively, the syringe 11 could be filled and actuated independently and the biasing means actuated by opening control 47 and moving abutment member 25 away from slidable driver 26. The preloaded syringe 11 would then be placed in syringe carrier 23 and carrier operated as previously indicated.

It will be appreciated that if desired, a means of measuring the amount of fluid 70 delivered through needle 54 can be provided. This is illustrated in FIG. 6 and can be in the form of a linear motion potentiometer 72, the slidable arm 73 of which will be secured to abutment member 25 by means of connector 68 fastened to block 35. As abutment member 25 pushes plunger rod 18 into barrel member 12, its travel will be measured by potentiometer shaft 73 which measurement will be indicated on qauge 71 as an indication of fluid delivery.

In the foregoing description, a flow control means 47 is described. The preferred unit is of the variable restrictor or needle valve type and operable by a thumb-type screw. It can be obtained from the Air Logic Division of the Fred Knapp Engraving Co., Inc., Racine, Wis. The rotatable retracting members 36 and 37 are spiral spring fitted about a spool. As they uncoil, an axle loading is created. These spiral coil springs are of the constant force type and are important in providing a constant force throughout the entire length of travel of abutment member 25. In the previous description, two such spiral coil springs 33 and 34 are indicated for use in conjunction with two retractable members 36 and 37. If desired, additional spring members could be added, as well as retractable members, depending upon the force desired to activate the syringe. These could be conveniently positioned in tandem by an extension of bracket 38 parallel to the syringe barrel. Pairs of spiral coil springs would be placed in alignment and all of them fastened to the block portions 32 and 35 by screws 41.

While not illustrated and, if desired, a support means could be provided for syringe carrier 23. This could be in the form of an envelope box having suitable supporting surface so that syringe tip or nozzle 16 would extend therefrom.

It will thus be seen that through the present invention there is now provided a syringe unit for the delivery of the contents of a syringe at a slow, uniform rate wherein the syringe can be of the standard type and readily accommodated in a syringe carrier member. The carrier member employs relatively few parts and readily accommodates the syringe therein. The delivery rate of the syringe is accommodated by an external flow control unit which is easily adjusted. The syringe carrier member is durable and of a rugged construction so as to be operable over a long period of time.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A syringe device for delivery of the contents thereof at a slow, uniform rate comprising:
   a syringe including:
   a barrel member defining a substantially tubular chamber having an internal wall portion and a nozzle portion;
   a plunger member having a sealing member secured thereto at one end and an engagement portion at the other, said sealing member in slidable engagement with said internal wall portion and said plunger member positioned for reciprocal movement in and out of said barrel member;
   engagement surfaces extending from said barrel member;
   a syringe carrier member including:
   an abutment member for contact with said engagement portion of said plunger member;
   a driver member constructed and arranged for contact with said engagement surfaces of said barrel member opposite said abutment member;
   two oppositely positioned guide means slidably associated with said driver member and extending longitudinally of said barrel member;
   two oppositely positioned negator biasing means operatively extending between said driver member and said carrier abutment member;
   control means of the fluid passage type defined by a variable restrictor operatively associated with said nozzle portion; and
   a length of tubing extending from said control means opposite said nozzle portion;
   whereby upon placement of a portion of said plunger member out of said syringe barrel and movement of said carrier abutment member away from said driver member said biasing means will be placed under tension; placement of said syringe in said syringe carrier member and upon closing of said control means, said fluid material will be retained in said syringe barrel, and upon opening of said control means, said carrier driver member and said carrier abutment surface will be forced in opposing directions to thereby move said plunger sealing member toward said nozzle portion to expel said fluid material from said barrel member and out through said tubing at a slow steady rate.

2. The syringe device as defined in claim 1 wherein said negator biasing means is of the spiral coiled spring type.

3. The syringe device as defined in claim 2 wherein said negator biasing means includes rotatable retracting members operatively associated with said driver member, said spiral coiled springs being operatively secured to said rotatable retracting members and fastened to said carrier abutment member.

4. The syringe device as defined in claim 1 wherein said guide means includes oppositely positioned rod members extending from said carrier abutment member, said driver member includes bearing surfaces for slidable contact with said rod members and said rod members are interconnected at their ends opposite said carrier abutment by means of a stabilizer member having an open portion to accommodate said syringe barrel.

5. The syringe device as defined in claim 1 wherein said control means is of the manually operable type including a rotatable control knob.

6. The syringe device as defined in claim 5 further including a hypodermic needle secured to said tubing at an end opposite said control means.

7. The syringe device as defined in claim 1 wherein said driver member includes a removable retainer member for accommodating said barrel member in said driver member and for affording contact with one of said engagement surfaces on said barrel member.

8. The syringe device as defined in claim 1 wherein said plunger member includes a rod portion.

* * * * *